United States Patent

Nabika et al.

Patent Number: 5,965,758
Date of Patent: Oct. 12, 1999

[54] METHOD FOR PRODUCING BRIDGED TYPE TRANSITION METAL COMPLEX

[75] Inventors: Masaaki Nabika, Ichihara; Kotohiro Nomura, Ikoma, both of Japan

[73] Assignee: Sumitomo Chemical Company, Limited, Osaka, Japan

[21] Appl. No.: 09/099,306

[22] Filed: Jun. 18, 1998

[30] Foreign Application Priority Data

Jun. 19, 1997 [JP] Japan ..................... 9-162673

[51] Int. Cl.$^6$ .............................. C07F 17/00; C07F 7/00
[52] U.S. Cl. ................. 556/11; 556/12; 556/22; 556/28; 556/53; 502/103; 502/117; 526/127; 526/160; 526/943
[58] Field of Search ................. 556/11, 12, 22, 556/28, 53; 502/103, 117; 526/127, 160, 943

[56] References Cited

U.S. PATENT DOCUMENTS

| | | | |
|---|---|---|---|
| 5,264,405 | 11/1993 | Canich | 502/103 |
| 5,532,394 | 7/1996 | Rosen et al. | 556/11 |
| 5,539,068 | 7/1996 | Devore et al. | 526/126 |
| 5,621,126 | 4/1997 | Canich et al. | 556/9 |
| 5,621,127 | 4/1997 | Langhauser et al. | 556/11 |
| 5,631,391 | 5/1997 | Canich | 556/11 |
| 5,688,880 | 11/1997 | Spencer et al. | 526/127 |
| 5,703,257 | 12/1997 | Rosen et al. | 556/7 |
| 5,723,398 | 3/1998 | Rosen et al. | 502/103 |

FOREIGN PATENT DOCUMENTS

| | | |
|---|---|---|
| 0 420 436 A1 | 4/1991 | European Pat. Off. . |
| 0601830A2 | 6/1994 | European Pat. Off. . |
| 0639579A2 | 2/1995 | European Pat. Off. . |
| 5505593 | 8/1993 | Japan . |
| 05230123 | 9/1993 | Japan . |
| 07501846 | 2/1995 | Japan . |
| 0753618 | 2/1995 | Japan . |
| 08239412 | 9/1996 | Japan . |
| WO9519984 | 7/1995 | WIPO . |

*Primary Examiner*—Porfirio Nazario-Gonzalez
*Attorney, Agent, or Firm*—Birch, Stewart, Kolasch & Birch, LLP

[57] ABSTRACT

A method for producing a bridged type transition metal complex represented by the following formula (1), comprising the following steps (i) and (ii):

step (i); a step for reacting a specific cyclopentadiene compound with an organic alkaline metal compound or an organomagnesium compound to produce an alkaline metal salt compound or a magnesium salt compound of the cyclopentadiene compound; and step (ii); a step for reacting the alkaline metal salt compound or magnesium salt compound of the cyclopentadiene compound with a specific transition metal compound, wherein at least the step (ii) is performed in the presence of an amine compound.

According to the present invention, there can be provided a method for producing a bridged type transition metal complex having one cyclopentadiene type anion skeleton on an industrial scale in high yield without requiring an industrially disadvantageous low temperature and replacement of the solvent, which is capable of reducing the number of the steps.

20 Claims, No Drawings

METHOD FOR PRODUCING BRIDGED TYPE TRANSITION METAL COMPLEX

BACKGROUND OF THE INVENTION

1. Field of the Invention

The present invention relates to a method for producing a bridged type transition metal complex. More particularly, it relates to a method for producing a bridged type transition metal complex having one group with a cyclopentadiene anion skeleton, which is useful as a catalyst component for olefin polymerization.

2. Description of the Related Arts

Transition metal complexes having a group (Cp) with a cyclopentadiene anion skeleton are effective as a catalyst for various organic synthesis reactions, and have widely used and studied at present. Among them, a complex containing an early transition metal such as titanium and zirconium is efficient as a catalyst component for olefin polymerization, and its study including practical use has widely been studied.

Particularly, WO9308199 and U.S. Pat. No. 5,096,867 disclose that a catalyst for olefin polymerization comprising, as a main component, a bridged type mono-Cp complex represented by the following structural formula, such as dimethylsilylene(tetramethylcyclopentadienyl) (tert-butylamide)titanium dichloride shows high activity. However, it is generally difficult to produce such a complex having a complicated structure, and the difficulty of the production was an obstacle in case of using the complex industrially.

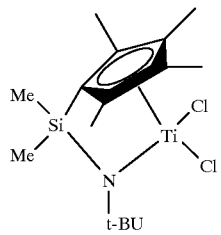

As the method of producing such a bridged type mono-Cp complex, particularly dimethylsilylene (tetramethylcyclopentadienyl)(tert-butylamide)titanium dichloride [Me$_2$Si(C$_5$Me$_4$)(NtBu)TiCl$_2$], JP-A-07-053618, JP-A-05-505593 and EP-A-601830 disclose a method of reacting a diethyl ether or tetrahydrofuran complex of titanium tetrachloride, which is prepared in the system under freezing at low temperature or separately synthesized and isolated, with [Me$_2$Si(C$_5$Me$_4$)(NtBu)]Li$_2$, which is separately synthesized and isolated from [Me$_2$Si(C$_5$Me$_4$H) (NHtBu)], in tetrahydrofuran or diethyl ether at low temperature.

However, this method has a problem that the yield of the desired complex is low and that it is difficult to handle [Me$_2$Si(C$_5$Me$_4$)(NtBu)]Li$_2$ isolated as a intermediate because it is considerably sensitive to moisture and oxygen in the air and has flammable.

In this method, a solvent such as diethyl ether, tetrahydrofuran or the like, is used to enhance the solubility of a lithium salt compound as the intermediate. Therefore, it was necessary that a complex of titanium tetrachloride with diethyl ether or tetrahydrofuran was previously prepared. Such a complex-forming reaction is a vigorous exothermic reaction and is normally carried out under freezing at low temperature, and should be avoided in the industrial production. Besides, the solubility of the complex thus obtained in diethyl ether or tetrahydrofuran is not sufficiently high. Moreover, since salts produced as by-products after the reaction, such as LiCl, etc. are soluble in these solvents, it is sometimes difficult to remove them by filtration. When a trial for obtaining the desired product by crystallization without removing these salts is made, a mixture of the desired product and the salts is sometimes obtained. Therefore, it is necessary to separate the desired product from the salts by a method of evaporating the solvent from the reaction solution, followed by solvent replacement with an aliphatic hydrocarbon solvent, an aromatic hydrocarbon solvent, etc. So, the synthesis method still has a problem to be solved in view of efficiency.

In addition, JP-A-07-053618, JP-A-05-230123 and EP-A-639579 disclose a method of reacting a tetrahydrofuran complex of titanium trichloride with the above lithium salt compound or a magnesium salt compound, [Me$_2$Si(C$_5$Me$_4$) (NtBu)](MgCl)$_2$(THF), which has been separately synthesized and isolated by the reaction between [Me$_2$Si(C$_5$Me$_4$H) (NHt-Bu)] and a Grignard reagent (i-PrMgCl), and oxidation-treating the reaction product with a small amount of dichloromethane, carbon tetrachloride, decyl chloride or silver chloride.

Furthermore, WO95/19984 discloses a method of synthesizing the desired complex by reacting a tetraalkoxytitanium with the above magnesium salt compound and treating the reaction product with silicon tetrachloride, boron trichloride or diethylaluminum chloride.

However, with respect to these methods, it could not be said that the yield is sufficiently high. Also, the following problems still remain. That is, when the number of steps is large or the reaction is performed via a lithium salt compound, there arises the same problem as that is described above. When a Grignard reagent is used, the yield of the magnesium salt compound as an intermediate is not sufficient (about 65%) and an isolating operation is required. Since the ether solvent is used, there is required a step of separating LiCl, MgCl$_2$, etc. formed as by-products after the reaction by using a method of solvent replacement.

Generally, in the construction of an industrial production process, the isolation of the intermediate can be omitted and the reaction at low temperature near −78 or −40° C. should be avoided because of causing the limitation of using used materials for the device and a high cost for equipment such as coolant. Furthermore, a method of producing the product efficiently in a short time using as little solvent replacement as possible is preferable. As described above, conventional methods showed insufficient yield and still had various problems to be solved in the case of carrying out the method on an industrial scale.

SUMMARY OF THE INVENTION

An object of the present invention is to provide a method for producing a bridged type transition metal complex having one cyclopentadiene type anion skeleton on an industrial scale in high yield without requiring an industrially disadvantageous low temperature and replacement of the solvent, which is capable of reducing the number of the steps.

The present inventors have intensively studied the above problems. As a result, they have found a method of forming a complex in the presence of an amine compound. Thus, the present invention has been accomplished.

The present invention provides a method for producing a bridged type transition metal complex represented by the following general formula (1) comprising the following steps (i) and (ii), wherein at least the step (ii) is performed in the presence of an amine compound.

step (i): a step for reacting a cyclopentadiene compound represented by the following general formula (2) with a compound selected from the group consisting of organo-alkaline metal compounds, hydrides of alkaline metal and organomagnesium compounds to produce an alkaline metal salt compound or a magnesium salt compound of the cyclopentadiene compound, and step (ii): a step for reacting said alkaline metal salt compound or magnesium salt compound of said cyclopentadiene compound with a transition metal compound represented by the following general formula (3);

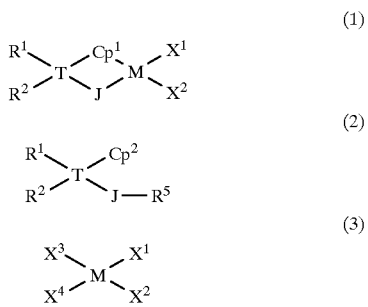

(wherein M represents a transition metal atom of Group IV of the Periodic Table of the Elements; J represents —O—, —S—, —NR$^3$— or —PR$^4$— (wherein R$^3$ and R$^4$ independently represent a hydrogen atom, an alkyl group having 1 to 20 carbon atoms optionally substituted with a halogen, vinyl group, an alkoxy group having 1 to 20 carbon atoms, an aralkyloxy group having 7 to 20 carbon atoms or an aryloxy group having 6 to 20 carbon atoms, an aralkyl group having 7 to 20 carbon atoms optionally substituted with a halogen, vinyl group, an alkoxy group having 1 to 20 carbon atoms, an aralkyloxy group having 7 to 20 carbon atoms or an aryloxy group having 6 to 20 carbon atoms, an aryl group having 6 to 20 carbon atoms optionally substituted with a halogen, vinyl group, an alkoxy group having 1 to 20 carbon atoms, an aralkyloxy group having 7 to 20 carbon atoms or an aryloxy group having 6 to 20 carbon atoms, or a silyl group having 1 to 20 carbon atoms optionally substituted with a halogen, vinyl group, an alkoxy group having 1 to 20 carbon atoms, an aralkyloxy group having 7 to 20 carbon atoms or an aryloxy group having 6 to 20 carbon atoms,; T represents an atom of Group XIV of the Periodical Table of the Elements; Cp$^1$ represents a group having a cyclopentadiene type anion skeleton; X$^1$, X$^2$, X$^3$, X$^4$, R$^1$ and R$^2$ independently represent a hydrogen atom, a halogen atom, an alkyl group having 1 to 20 carbon atoms optionally substituted with a halogen, vinyl group, an alkoxy group having 1 to 20 carbon atoms, an aralkyloxy group having 7 to 20 carbon atoms or an aryloxy group having 6 to 20 carbon atoms, an aralkyl group having 7 to 20 carbon atoms optionally substituted with a halogen, vinyl group, an alkoxy group having 1 to 20 carbon atoms, an aralkyloxy group having 7 to 20 carbon atoms or an aryloxy group having 6 to 20 carbon atoms, an aryl group having 6 to 20 carbon atoms optionally substituted with a halogen, vinyl group, an alkoxy group having 1 to 20 carbon atoms, an aralkyloxy group having 7 to 20 carbon atoms or an aryloxy group having 6 to 20 carbon atoms, a silyl group having 1 to 20 carbon atoms optionally substituted with a halogen, vinyl group, an alkoxy group having 1 to 20 carbon atoms, an aralkyloxy group having 7 to 20 carbon atoms or an aryloxy group having 6 to 20 carbon atoms, an alkoxy group having 1 to 20 carbon atoms optionally substituted with a halogen, vinyl group, an alkoxy group having 1 to 20 carbon atoms, an aralkyloxy group having 7 to 20 carbon atoms or an aryloxy group having 6 to 20 carbon atoms, an aralkyloxy group having 7 to 20 carbon atoms optionally substituted with a halogen, vinyl group, an alkoxy group having 1 to 20 carbon atoms, an aralkyloxy group having 7 to 20 carbon atoms or an aryloxy group having 6 to 20 carbon atoms, an aryloxy group having 6 to 20 carbon atoms optionally substituted with a halogen, vinyl group, an alkoxy group having 1 to 20 carbon atoms, an aralkyloxy group having 7 to 20 carbon atoms or an aryloxy group having 6 to 20 carbon atoms, a sulfonyloxy group having 1 to 20 carbon atoms or a di-substituted amino group having 2 to 20 carbon atoms; provided that X$^1$ and X$^2$ and/or R$^1$ and R$^2$ may optionally combine with each other to form a ring; Cp$^2$ represents a group having a cyclopentadiene skeleton; R$^5$ represents a hydrogen atom, an alkyl group having 1 to 20 carbon atoms optionally substituted with a halogen, vinyl group, an alkoxy group having 1 to 20 carbon atoms, an aralkyloxy group having 7 to 20 carbon atoms or an aryloxy group having 6 to 20 carbon atoms, an aralkyl group having 7 to 20 carbon atoms optionally substituted with a halogen, vinyl group, an alkoxy group having 1 to 20 carbon atoms, an aralkyloxy group having 7 to 20 carbon atoms or an aryloxy group having 6 to 20 carbon atoms, an aryl group having 6 to 20 carbon atoms optionally substituted with a halogen, vinyl group, an alkoxy group having 1 to 20 carbon atoms, an aralkyloxy group having 7 to 20 carbon atoms or an aryloxy group having 6 to 20 carbon atoms or a silyl group having 1 to 20 carbon atoms optionally substituted with a halogen, vinyl group, an alkoxy group having 1 to 20 carbon atoms, an aralkyloxy group having 7 to 20 carbon atoms or an aryloxy group having 6 to 20 carbon atoms).

The present invention will be described in detail below.

DETAILED DESCRIPTION OF THE INVENTION

The transition metal atom represented by M in the general formulas (1) and (3) is a transition metal atom of Group IV of the Periodic Table of Elements (IUPAC Inorganic Chemistry Nomenclature, revised edition, 1989) and examples thereof include titanium atom, zirconium atom, hafnium atom, etc.

The group having a cyclopentadiene type anion skeleton, which is represented by Cp$^1$ of the general formula (1), is preferably a $\eta^5$-(substituted)cyclopentadienyl group, $\eta^5$-(substituted)indenyl group or $\eta^5$-(substituted)fluorenyl group, and specific examples thereof includes $\eta^5$-cyclopentadienyl group, $\eta^5$-methylcyclopentadienyl group, $\eta^5$-dimethylcyclopentadienyl group, $\eta^5$-trimethylcyclopentadienyl group, $\eta^5$-tetramethylcyclopentadienyl group, $\eta^5$-trimethylcyclopentadienyl group, $\eta^5$-ethylcyclopentadienyl group, $\eta^5$-n-propylcyclopentadienyl group, $\eta^5$-di-n-propylcyclopentadienyl group, $\eta^5$-isopropylcyclopentadienyl group, $\eta^5$-diisopropylcyclopentadienyl group, $\eta^5$-butylcyclopentadienyl group, $\eta^5$-di-n-butylcyclopentadienyl group, $\eta^5$-sec-butylcyclopentadienyl group, $\eta^5$-di-sec-butylcyclopentadienyl group, $\eta^5$-tert-butylcyclopentadienyl group, $\eta^5$-di-tert-butylcyclopentadienyl group, $\eta^5$-n-pentylcyclopentadienyl group, $\eta^5$-neopentylcyclopentadienyl group, $\eta^5$-n-hexylcyclopentadienyl group, $\eta^5$-n-octylcyclopentadienyl group, $\eta^5$-phenylcyclopentadienyl group, $\eta^5$-naphthylcyclopentadienyl group, $\eta^5$-trimethylsilylcyclopentadienyl group, $\eta^5$-triethylsilylcyclopentadienyl group, $\eta^5$-butyldimethylsilylcyclopentadienyl group, $\eta^5$-indenyl group, $\eta^5$-methylindenyl group, $\eta^5$-dimethylindenyl group, $\eta^5$-ethylindenyl group, $\eta^5$-n-propylindenyl group, $\eta^5$-isopropylindenyl group, $\eta^5$-n-butylindenyl group, $\eta^5$-sec-butylindenyl group, $\eta^5$-tert-butylindenyl group, $\eta^5$-pentylindenyl group, $\eta^5$-neopentylindenyl group, $\eta^5$-n-hexylindenyl group, $\eta^5$-n-octylindenyl group, $\eta^5$-n-decylindenyl group, $\eta^5$-phenylindenyl group, $\eta^5$-methylphenylindenyl group, $\eta^5$-naphthylindenyl group, $\eta^5$-trimethylsilylindenyl group, $\eta^5$-triethylsilylindenyl group, $\eta^5$-tert-butyldimethylsilylindenyl group, $\eta^5$-tetrahydroindenyl group, $\eta^5$-fluorenyl group, $\eta^5$-methylfluorenyl group, $\eta^5$-dimethylfluorenyl group, $\eta^5$-ethylfluorenyl group, $\eta^5$-diethylfluorenyl group, $\eta^5$-n-propylfluorenyl group, $\eta^5$-di-n-propylfluorenyl group, $\eta^5$-isopropylfluorenyl group, $\eta^5$-diisopropylfluorenyl group, $\eta^5$-n-butylfluorenyl group, $\eta^5$-sec-butylfluorenyl group, $\eta^5$-tert-butylfluorenyl group, $\eta^5$-di-n-butyl luorenyl group, $\eta^5$-di-sec-butylfluorenyl group, $\eta^5$-di-tert-butylfluorenyl group, $\eta^5$-n-pentylfluorenyl group, $\eta^5$-neopentylfluorenyl group, $\eta^5$-n-hexylfluorenyl group, $\eta^5$-n-octylfluorenyl group, $\eta^5$-n-decylfluorenyl group, $\eta^5$-n-dodecylfluorenyl group, $\eta^5$-phenylfluorenyl group, $\eta^5$-di-phenylfluorenyl group, $\eta^5$-methylphenylfluorenyl group, $\eta^5$-naphthylfluorenyl group, $\eta^5$-trimethylsilylfluorenyl group, $\eta^5$-bis-trimethylsilylfluorenyl group, $\eta^5$-triethylsilylfluorenyl group, $\eta^5$-tert-butyldimethylsilylfluorenyl group, etc.

Particularly, $\eta^5$-cyclopentadienyl group, $\eta^5$-methylcyclopentadienyl group, $\eta^5$-dimethylcyclopentadienyl group, $\eta^5$-tetramethylcyclopentadienyl group, $\eta^5$-tert-butylcyclopentadienyl group, $\eta^5$-di-tert-butylcyclopentadienyl group, $\eta^5$-indenyl group, $\eta^5$-fluorenyl group are preferred.

The substituents $X^1$, $X^2$, $X^3$, $X^4$, $R^1$ and $R^2$ of the general formulas (1) to (3) independently represent a hydrogen atom, a halogen atom, an optionally substituted alkyl group having 1 to 20 carbon atoms, an optionally substituted aralkyl group having 7 to 20 carbon atoms, an optionally substituted aryl group having 6 to 20 carbon atoms, an optionally substituted silyl group having 1 to 20 carbon atoms, an optionally substituted alkoxy group having 1 to 20 carbon atoms, optionally substituted aralkyloxy group having 7 to 20 carbon atoms, an optionally substituted aryloxy group having 6 to 20 carbon atoms, an optionally substituted sulfonyloxy group having 1 to 20 carbon atoms or a di-substituted amino group having 2 to 20 carbon atoms; provided that $X^1$ and $X^2$ and/or $R^1$ and $R^2$ may optionally combine with each other to form a ring.

Examples of the halogen atom in the substituents $X^1$, $X^2$, $X^3$, $X^4$, and $R^2$ of the general formulas (1) to (3) include fluorine atom, chlorine atom, bromine atom and iodine atom, preferably chlorine atom and bromine atom.

The alkyl group having 1 to 20 carbon atoms in the substituents $X^1$, $X^2$, $X^3$, $X^4$, $R^1$ and $R^2$ of the general formulas (1) to (3) includes methyl group, ethyl group, n-propyl group, isopropyl group, n-butyl group, sec-butyl group, tert-butyl group, n-pentyl group, neopentyl group, amyl group, n-hexyl group, n-octyl group, n-decyl group, n-dodecyl group, n-pentadecyl group, n-eicosyl group, etc., preferably methyl group, ethyl group, isopropyl group, tert-butyl group and amyl group.

All of these alkyl groups may be substituted with a halogen atom such as fluorine atom, chlorine atom, bromine atom, iodine atom; an alkoxy group having 1 to 20 carbon atoms such as methoxy group, ethoxy group; or an aryloxy group having 6 to 20 carbon atoms such as phenoxy group; an aralkyloxy group having 7 to 20 carbon atoms such as benzyloxy. The alkyl group having 1 to 20 carbon atoms, which is substituted with a halogen atom, includes fluoromethyl group, difluoromethyl group, trifluoromethyl group, chloromethyl group, dichloromethyl group, trichloromethyl group, bromomethyl group, dibromomethyl group, tribromomethyl group, iodomethyl group, diiodomethyl group, triiodomethyl group, fluoroethyl group, difluoroethyl group, trifluoroethyl group, tetrafluoroethyl group, pentafluoroethyl group, chloroethyl group, dichloroethyl group, trichloroethyl group, tetrachloroethyl group, pentachloroethyl group, bromoethyl group, dibromoethyl group, tribromoethyl group, tetrabromoethyl group, pentabromoethyl group, perfluoropropyl group, perfluorobutyl group, perfluoropentyl group, perfluorohexyl group, perfluorooctyl group, perfluorododecyl group, perfluoropentadecyl group, perfluoroeicosyl group, perchloropropyl group, perchlorobutyl group, perchloropentyl group, perchlorohexyl group, perchlorooctyl group, perchlorododecyl group, perchloropentadecyl group, perchloroeicosyl group, perbromopropyl group, perbromobutyl group, perbromopentyl group, perbromohexyl group, perbromooctyl group, perbromododecyl group, perbromopentadecyl group, perbromoeicosyl group, etc.

The aralkyl group having 7 to 20 carbon atoms in the substituents $X^1$, $X^2$, $X^3$, $X^4$, $R^1$ and $R^2$ of the general formulas (1) to (3) includes benzyl group, (2-methylphenyl)methyl group, (3-methylphenyl)methyl group, (4-methylphenyl) methyl group, (2,3-dimethylphenyl) methyl group, (2,4-dimethylphenyl)methyl group, (2,5-dimethylphenyl)methyl group, (2,6-dimethylphenyl)methyl group, (3,4-dimethylphenyl)methyl group, (4,6-dimethylphenyl)methyl group, (2,3,4-trimethylphenyl) methyl group, (2,3,5-trimethylphenyl)methyl group, (2,3,6-trimethylphenyl) methyl group, (3,4,5-trimethylphenyl) methyl group, (2,4,6-trimethylphenyl)methyl group, (2,3,4,5-tetramethylphenyl)methyl group, (2,3,4,6-tetramethylphenyl)methyl group, (2,3,5,6-tetramethylphenyl)methyl group, (pentamethylphenyl) methyl group, (ethylphenyl)methyl group, (n-propylphenyl) methyl group, (isopropylphenyl)methyl group, (n-butylphenyl)methyl group, (sec-butylphenyl)methyl group, (tert-butylphenyl)methyl group, (n-pentylphenyl) methyl group, (neopentylphenyl)methyl group, (n-hexylphenyl)methyl group, (n-octylphenyl)methyl group, (n-decylphenyl)methyl group, (n-decylphenyl)methyl group, (n-tetradecylphenyl)methyl group, naphthylmethyl group, anthracenylmethyl group, etc., preferably benzyl group.

All of these aralkyl groups may be substituted with a halogen atom such as fluorine atom, chlorine atom, bromine atom, iodine atom; an alkoxy group having 1 to 20 carbon atoms such as methoxy group, ethoxy group; or an aryloxy group having 6 to 20 carbon atoms such as phenoxy group; an aralkyloxy group having 7 to 20 carbon atoms such as benzyloxy.

The aryl group having 6 to 20 carbon atoms in the substituents $X^1$, $X^2$, $X^3$, $X^4$, $R^1$ and $R^2$ of the general formulas (1) to (3) includes phenyl group, 2-tolyl group, 3-tolyl group, 4-tolyl group, 2,3-xylyl group, 2,4-xylyl group, 2,5-xylyl group, 2,6-xylyl group, 3,4-xylyl group, 3,5-xylyl group, 2,3,4-trimethylphenyl group, 2,3,5-trimethylphenyl group, 2,3,6-trimethylphenyl group, 2,4,6-trimethylphenyl group, 3,4,5-trimethylphenyl group, 2,3,4,5-tetramethylphenyl group, 2,3,4,6-tetramethylphenyl group, 2,3,5,6-tetramethylphenyl group, pentamethylphenyl group, ethylphenyl group, n-propylphenyl group, isopropylphenyl group, n-butylphenyl group, sec-butylphenyl group, tert-butylphenyl group, n-pentylphenyl group, neopentylphenyl group, n-hexylphenyl group, n-octylphenyl group, n-decylphenyl group, n-dodecylphenyl group, n-tetradecylphenyl group, naphthyl group, anthracenyl group, etc., preferably phenyl group. All of these aryl groups may be substituted with a halogen atom such as fluorine atom, chlorine atom, bromine atom, iodine atom; an alkoxy group having 1 to 20 carbon atoms such as methoxy group, ethoxy group; or an aryloxy group having 6 to 20 carbon atoms such as phenoxy group; an aralkyloxy group having 7 to 20 carbon atoms such as benzyloxy.

The silyl group having 1 to 20 carbon atoms in the substituents $X^1$, $X^2$, $X^3$, $X^4$, $R^1$ and $R^2$ of the general formulas (1) to (3) is a silyl group substituted with a hydrocarbon, and hydrocarbon includes alkyl group having 1 to 10 carbon atoms such as methyl group, ethyl group, n-propyl group, isopropyl group, n-butyl group, sec-butyl group, tert-butyl group, isobutyl group, n-pentyl group, n-hexyl group, cyclohexyl group, etc.; and aryl group such as phenyl group. The silyl group having 1 to 20 carbon atoms includes 1-substituted silyl group having 1 to 20 carbon atoms such as methylsilyl group, ethylsilyl group, phenylsilyl group; di-substituted silyl group having 2 to 20 carbon such as dimethylsilyl group, diethylsilyl group, diphenylsilyl group; and tri-substituted silyl group having 3 to 20 carbon atoms such as trimethylsilyl group, triethylsilyl group, tri-n-propylsilyl group, triisopropylsilyl group, tri-n-butylsilyl group, tri-sec-butylsilyl group, tri-tert-butylsilyl group, tri-isobutylsilyl group, tert-butyl-dimethylsilyl group, tri-n-pentylsilyl group, tri-n-hexylsilyl group, tricyclohexylsilyl group, triphenylsilyl group; preferably tri-substituted silyl group having 3 to 20 carbon atoms. Particularly, trimethylsilyl group, tert-butyldimethylsilyl group and triphenylsilyl group are preferred. The hydrocarbon group of all of these silyl groups may be substituted with a halogen atom such as fluorine atom, chlorine atom, bromine atom, iodine atom; an alkoxy group having 1 to 20 carbon atoms such as methoxy group, ethoxy group; or an aryloxy group having 6 to 20 carbon atoms such as phenoxy group; an aralkyloxy group having 7 to 20 carbon atoms such as benzyloxy.

The alkoxy group having 1 to 20 carbon atoms in the substituents $X^1$, $X^2$, $X^3$, $X^4$, $R^1$ and $R^2$ of the general formulas (1) to (3) include methoxy group, ethoxy group, n-propoxy group, isopropoxy group, n-butoxy group, sec-butoxy group, t-butoxy group, n-pentoxy group, neopentoxy group, n-hexoxy group, n-octoxy group, n-dodesoxy group, n-pentadesoxy group, n-icosoxy group, etc.; preferably methoxy group, ethoxy group and t-butoxy group.

All of these alkoxy groups may be substituted with a halogen atom such as fluorine atom, chlorine atom, bromine atom, iodine atom; an alkoxy group having 1 to 20 carbon atoms such as methoxy group, ethoxy group; or an aryloxy group having 6 to 20 carbon atoms such as phenoxy group; an aralkyloxy group having 7 to 20 carbon atoms such as benzyloxy.

The aralkyloxy group having 7 to 20 carbon atoms in the substituents $X^1$, $X^2$, $X^3$, $X^4$, $R^1$ and $R^2$ of the general formulas (1) to (3) includes benzyloxy group, (2-methylphenyl)methoxy group, (3-methylphenyl)methoxy group, (4-methylphenyl)methoxy group, (2,3-dimethylphenyl)methoxy group, (2,4-dimethylphenyl)methoxy group, (2,5-dimethylphenyl)methoxy group, (2,6-dimethylphenyl)methoxy group, (3,4-dimethylphenyl)methoxy group, (3,5-dimethylphenyl)methoxy group, (2,3,4-trimethylphenyl)methoxy group, (2,3,5-trimethylphenyl)methoxy group, (2,3,6-trimethylphenyl)methoxy group, (2,4,5-trimethylphenyl)methoxy group, (2,4,6-trimethylphenyl)methoxy group, (3,4,5-trimethylphenyl)methoxy group, (2,3,4,5-tetramethylphenyl)methoxy group, (2,3,4,6-tetramethylphenyl)methoxy group, (2,3,5,6-tetramethylphenyl)methoxy group, (pentamethylphenyl)methoxy group, (ethylphenyl)methoxy group, (n-propylphenyl)methoxy group, (isopropylphenyl)methoxy group, (n-butylphenyl)methoxy group, (sec-butylphenyl)methoxy group, (tert-butylphenyl)methoxy group, (n-hexylphenyl)methoxy group, (n-octylphenyl)methoxy group, (n-decylphenyl)methoxy group, (n-tetradecylphenyl)methoxy group, naphthylmethoxy group, anthracenylmethoxy group, etc., preferably benzyloxy group.

All of these aralkyloxy groups may be substituted with a halogen atom such as fluorine atom, chlorine atom, bromine atom, iodine atom; an alkoxy group having 1 to 20 carbon atoms such as methoxy group, ethoxy group; or an aryloxy group having 6 to 20 carbon atoms such as phenoxy group; an aralkyloxy group having 7 to 20 carbon atomssuch as benzyloxy.

The aryloxy group having 6 to 20 carbon atoms in the substituents $X^1$, $X^2$, $X^3$, $X^4$, $R^1$ and $R^2$ of the general formulas (1) to (3) includes phenoxy group, 2-methylphenoxy group, 3-methylphenoxy group, 4-methylphenoxy group, 2,3-dimethylphenoxy group, 2,4-dimethylphenoxv group, 2,5-dimethylphenoxy group, 2,6-dimethylphenoxy group, 3,4-dimethylphenoxy group, 3,5-dimethylphenoxy group, 2,3,4-trimethylphenoxy group, 2,3,5-trimethylphenoxy group, 2,3,6-trimethylphenoxy group, 2,4,5-trimethylphenoxy group, 2 4,6-trimethylphenoxy group, 3,4,5-trimethylphenoxy group, 2,3,4,5-tetramethylphenoxy group, 2,3,4,6-tetramethylphenoxy group, 2,3,5,6-tetramethylphenoxy group, pentamethylphenoxyl group, ethylphenoxy group, n-propylphenoxy group, isopropylphenoxy group, n-butylphenoxy group, sec-butylphenoxy group, tert-butylphenoxy group, n-hexylphenoxy group, n-octylphenoxy group, n-decylphenoxy group, n-tetradecylphenoxy group, naphthoxy group, anthracenoxy group, etc. All of these aryloxy groups may be substituted with a halogen atom such as fluorine atom, chlorine atom, bromine atom, iodine atom; an alkoxy group having 1 to 20 carbon atoms such as methoxy group, ethoxy group; or an aryloxy group having 6 to 20 carbon atoms such as phenoxy group; an aralkyloxy group having 7 to 20 carbon atoms such as benzyloxy.

The sulfonyloxy group having 1 to 20 carbon atoms in the substituents $X^1$, $X^2$, $X^3$, $X^4$, $R^1$ and $R^2$ of the general formulas (1) to (3) is a group having a sulfonate structure, and is preferably an alkylsulfonyloxy group having 1 to 20 carbon atoms, an aralkylsulfonyloxy group having 7 to 20 carbon atoms or an arylsulfonyloxy group having 6 to 20 carbon atoms. Specific example thereof include methylsulfonyloxy group ($CH_3SO_2$—O—), ethylsulfonyloxy group, phenylsulfonyloxy group , p-toluenesulfonyloxy group, etc.

The di-substituted amino group in the substituents $X^1$, $X^2$, $X^3$, $X^4$, $R^1$ and $R^2$ of the general formulas (1) to (3) is an amino group substituted with two hydrocarbon groups, and the hydrocarbon group includes alkyl group having 1 to 10 carbon atoms such as methyl group, ethyl group, n-propyl group, isopropyl group, n-butyl group, sec-butyl group, tert-butyl group, isobutyl group, n-pentyl group, n-hexyl group, cyclohexyl group; and aryl group such as phenyl group, etc. The di-substituted amino groups having 1 to 10 carbon atoms includes dimethylamino group, diethylamino group, di-n-propylamino group, diisopropylamino group, di-n-butylamino group, di-sec-butylamino group, di-tert-butylamino group, di-isobutylamino group, tert-butylisopropylamino group, di-n-hexylamino group, di-n-cylamino group, di-n-decylamino group, diphenylamino group, bistrimethylsilylamino group, bis-tert-butyldimethylsilylamino group, etc., preferably dimethylamino group and diethylamino group.

Each of the substituents $X^1$, $X^2$, $X^3$ and $X^4$ is preferably hydrogen atom, or the halogen atom, alkyl group, aralkyl group, silyl group, alkoxy group, aralkyloxy group, sulfonyloxy group or di-substituted amino group, more preferably the halogen atom, alkoxy group or di-substituted amino group. Particularly, the halogen atom is preferred.

The substituents $R^1$ and $R^2$ preferably represent hydrogen or the halogen atom, alkyl group, aryl group, aralkyl group, silyl group, alkoxy group or aralkyloxy group, more preferably the halogen atom, alkyl group or aryl group.

Mal in the general formulas (1) and (2) is a divalent group represented by —O—, —S—, —NR$^3$— or —PR$^4$—, wherein $R^3$ and $R^4$ independently represent a hydrogen atom, a halogen atom, an optionally substituted alkyl group having 1 to 20 carbon atoms, an optionally substituted aralkyl group having 7 to 20 carbon atoms, an optionally substituted aryl group having 6 to 20 carbon atoms or an optionally substituted silyl group having 1 to 20 carbon atoms.

The halogen atom, the optionally substituted alkyl group having 1 to 20 carbon atoms, the optionally substituted aralkyl group having 7 to 20 carbon atoms, the optionally substituted aryl group having 6 to 20 carbon atoms and the optionally substituted silyl group having 1 to 20 carbon atoms for $R^3$ and $R^4$ are same as those described with respect to the above substituents $X^1$, $X^2$, $X^3$, $X^4$, $R^1$ and $R^2$, preferably alkyl group.

"J" in the general formulas (1) and (2) is preferably a divalent group represented by —NR$^3$— or —PR$^4$—, more preferably a divalent group represented by —NR$^3$—.

"T" in the general formulas (1) and (2) represents an atom of Group 14 of the Periodic Table of the Elements, and T includes carbon atom, silicon atom, germanium atom, etc., preferably carbon atom or silicon atom.

"Cp$^2$" in the general formula (2) is a group having a cyclopentadiene skeleton, and is capable of giving a group having a cyclopentadiene type anion skeleton by reacting with a compound selected from the group consisting of organo-alkaline metal compounds, hydrides of alkaline metal and organomagnesium compounds. "Cp$^2$" sometimes include plural isomers derived from a difference in position of the substituent and position of a double bond in the cyclopentadiene skeleton, and all of these isomers are included in the present invention.

"R$^5$" in the general formula (2) is a hydrogen atom, an optionally substituted alkyl group having 1 to 20 carbon atoms, an aralkyl group having 7 to 20 carbon atoms optionally substituted with a halogen, vinyl group, an alkoxy group having 1 to 20 carbon atoms, an aralkyloxy group having 7 to 20 carbon atoms or an aryloxy group having 6 to 20 carbon atoms, an aryl group having 6 to 20 carbon atoms optionally substituted with a halogen, vinyl group, an alkoxy group having 1 to 20 carbon atoms, an aralkyloxy group having 7 to 20 carbon atoms or an aryloxy group having 6 to 20 carbon atoms or a silyl group having 1 to 20 carbon atoms optionally substituted with a halogen, vinyl group, an alkoxy group having 1 to 20 carbon atoms, an aralkyloxy group having 7 to 20 carbon atoms or an aryloxy group having 6 to 20 carbon atoms. The alkyl group having 1 to 20 carbon atoms, the aralkyl group having 7 to 20 carbon atoms, the aryl group having 6 to 20 carbon atoms and the silyl group having 1 to 20 carbon atoms for $R^5$ are the same as those described with respect to above substituents $X^1$, $X^2$, $X^3$, $X^4$, $R^1$ and $R^2$, preferably hydrogen atom or alkyl group.

Specific examples of the bridged type transition metal complex represented by the general formula (1) include compounds such as dimethylsilylene(methylamide) (cyclopentadienyl)titanium dichloride, dimethyl silylene (ethylamide)(cyclopentadienyl)titanium dichloride, dimethylsilylene(n-propylamide) (cyclopentadienyl) titanium dichloride, dimethylsilylene(isopropylamide) (cyclopentadienyl) titanium dichloride, dimethylsilylene (tert-butylamide) (cyclopentadienyl)titanium dichloride, dimethylsilylene(phenylamide)(cyclopentadienyl)-titanium dichloride, dimethylsilylene (cyclohexylamide) (cyclopentadienyl)titanium dichloride, dimethylsilylene (methylamide)(methylcyclopentadienyl) titanium dichloride, dimethylsilylene(ethylamide) (methylcyclopentadienyl)titanium dichloride, dimethylsilylene(n-propylamide) (methylcyclopentadienyl) titanium dichloride, dimethylsilylene(isopropylamide) (methylcyclopentadienyl) titanium dichloride, dimethylsilylene(tert-butylamide) (methylcyclopentadienyl)titanium dichloride, dimethylsilylene(phenylamide) (methylcyciopenvadienyl) titanium dichloride, dimethylsilylene(cyclohexylamide) (methylcyclopentadienyl)titanium dichloride, dimethylsilylene(methylamide)(dimethylcyclopentadienyl) titanium dichloride, dimethylsilylene(ethylamide) (dimethylcyclopentadienyl) titanium dichloride, dimethylsilylene(n-propylamide) (dimethylcyclopentadienyl)titanium dichloride, dimethylsilylene(isopropylamide) (dimethylcyclopentadienyl)titanium dichloride, dimethylsilylene(tert-butylamide) (dimethylcyclopentadienyl)titanium dichloride, dimethylsilylene(phenylamide)(dimethylcyclopentadienyl) titanium dichloride, dimethylsilylene(cyclohexylamide) (dimethylcyclopentadienyl)titanium dichloride, dimethylsilylene(methylamide)(trimethylcyclopentadienyl) titanium dichloride, dimethylsilylene(ethylamide) (trimethylcyclopentadienyl)titanium dichloride, dimethylsilylene(n-propylamide) (trimethylcyclopentadienyl)titanium dichloride, dimethylsilylene(isopropylamide) (trimethylcyclopentadienyl)titanium dichloride, dimethylsilylene(tert-butylamide) (trimethylcyclopentadienyl)titanium dichloride, dimethylsilylene(phenylamide)(trimethylcyclopentadienyl) titanium dichloride, dimethylsilylene(cyclohexylamide) (trimethylcyclopentadienyl)titanium dichloride, dimethylsilylene(methylamide) (tetramethylcyclopentadienyl) titanium dichloride, dimethylsilylene(ethylamide) (tetramethylcyclopentadienyl)titanium dichloride, dimethylsilylene(n-propylamide) (tetramethylcyclopentadienyl)titanium dichloride, dimethynium dichloride, dimethylsilylene(tert-butylamide) (tetramethylcyclopentadienyl)titanium dichloride, dimethylsilylene(phenylamide)

(tetramethylcyclopentadienyl)titanium dichloride, dimethylsilylene(cyclohexylamide) (tetramethylcyclopentadienyl)titanium dichloride, dimethylsilylene(methylamide) (ethylcyclopentadienyl) titanium dichloride, dimethylsilylene(ethylamide) (ethylcyclopentad-enyl) titanium dichloride, dimethylsilylene(n-propylamide) (ethylcyclopentadienyl) titanium dichloride, dimethylsilylene(isopropylamide) (ethylcyclopentadienyl) titanium dichloride, dimethylsilylene(tert-butylamide) (ethylcyclopentadienyl) titanium dichloride, dimethylsilylene(phenylamide) (ethylcyclopentadienyl) titanium dichloride, dimethylsilylene(cyclohexylamide) (ethylcyclopentadienyl) titanium dichloride, dimethylsilylene(methylamide)(n-propylcyclopentadienyl) titanium dichloride, dimethylsilylene(ethylamide) (n-propylcyclopentadienyl)titanium dichloride, dimethylsilylene(n-propylamide) (n-propylcyclopentadienyl)titanium dichloride, dimethylsilylene(isopropylamide) (n-propylcyclopentadienyl)titanium dichloride, dimethylsilylene(tert-butylamide) (n-propylcyclopentadienyl)titanium dichloride, dimethylsilylene(phenylamide) (n-propylcyclopentadienyl)titanium dichloride, dimethylsilylene(cyclohexylamide) (n-propylcyclopentadienyl)-titanium dichloride, dimethylsilylene(methylamide) (isopropylcyclopentadienyl)titanium dichloride, dimethylsilylene(ethylamide) (isopropylcyclopentadienyl) titanium dichloride, dimethylsilylene(n-propylamide) (isopropylcyclopentadienyl)titanium dichloride, dimethylsilylene(isopropylamide) (isopropylcyclopentadienyl)titanium dichloride, dimethylsilylene (tert-butylamide)(isopropylcyclopentadienyl) titanium dichloride, dimethylsilylene(phenylamide) (isopropylcyclopentadienyl)titanium dichloride, dimethylsilylene(cyclohexylamide) (isopropylcyclopentadienyl)titanium dichloride, dimethylsilylene(methylamide) (n-butylcyclopentadienyl) titanium dichloride, dimethylsilylene(ethylamide)(n-butylcyclopentadienyl) titanium dichloride, dimethylsilylene(n-propylamide) (n-butylcyclopentadienyl) titanium dichloride, dimethylsilylene(isopropylamide) (n-butylcyclopentadienyl)titanium dichloride, dimethylsilylene(tert-butylamide) (n-butylcyclopentadienyl)titanium dichloride, dimethylsilylene(phenylamide) (n-butylcyclopentadienyl) titanium dichloride, dimethylsilylene(cyclohexylamide) (n-butylcyclopentadienyl)titanium dichloride, dimethylsilylene(methylamide) (sec-butylcyclopentadienyl) titanium dichloride, dimethylsilylene(ethylamide) (sec-butylcyclopentadienyl)titanium dichloride, dimethylsilylene (n-propylamide) (sec-butylcyclopentadienyl)titanium dichloride, dimethylsilylene(isopropylamide) (sec-butylcyclopentadienyl)titanium dichloride, dimethylsilylene (tert-butylamide) (sec-butylcyclopentadienyl)titanium dichloride, dimethylsilylene(phenylamide) (sec-butylcyclopentadienyl)titanium dichloride, dimethylsilylene (cyclohexylamide) (sec-butylcyclopentadienyl)titanium dichloride, dimethylsilylene(methylamide) (isobutylcyclopentadienyl) titanium dichloride, dimethylsilylene(ethylamide) (isobutylcvclopentadienyl) titanium dichloride, dimethylsilylene(n-propylamide) (isobutylcyclopentadienyl)titanium dichloride, dimethylsilylene(isopropylamide) (isobutylcyclopentadienyl)titanium dichloride, dimethylsilylene(tert-butylamide) (isobutylcyclopentadienyl)titanium dichloride, dimethylsilylene(phenylamide)(isobutylcyclopentadienyl) titanium dichloride, dimethylsilylene(cyclohexylamide) (isobutylcyclopentadienyl)titanium dichloride, dimethylsilylene(methylamide) (tert-butylcyclopentadienyl)titanium dichloride, dimethylsilylene(ethylamide) (tert-butylcyclopentadienyl)titanium dichloride, dimethylsilylene (n-propylamide) (tert-butylcyclopentadienyl)titanium dichloride, dimethylsilylene(isopropylamide) (tert-butylcyclopentadienyl)titanium dichloride, dimethylsilylene (tert-butylamide) (tert-butylcyclopentadienyl)titanium dichloride, dimethylsilylene(phenylamide) (tert-butylcyclopentadienyl)titanium dichloride, dimethylsilylene (cyclohexylamide) (tert-butylcyclopentadienyl)titanium dichloride, dimethylsilylene(methylamide) (di-tert-butylcyclopentadienyl)titanium dichloride, dimethylsilylene (ethylamide) (di-tert-butylcyclopentadienyl)titanium dichloride, dimethylsilylene(n-propylamide) (di-tert-butyl-cyclopentadienyl)titanium dichloride, dimethyl-silylene (isopropylamide) (di-tert-butylcyclopentadienyl)titanium dichloride, dimethylsilylene(tert-butylamide) (di-tert-butylcyclopentadienyl)titanium dichloride, dimethylsilylene (phenylamide) (di-tert-butylcyclopentadienyl)titanium dichloride, dimethylsilylene(cyclohexylamide) (di-tert-butylcyclopentadienyi)titanium dichloride, dimethylsilylene (methylamide) (tert-butyldimethylsilylcyclopentadienyl) titanium dichloride, dimethylsilylene(ethylamide) (tert-butyldimethylsilylcyclopentadienyl)titanium dichloride, dimethylsilylene(n-propylamide) (tert-butyldimethylsilylcyclopentadienyl)titanium dichloride, dimethylsilylene(isopropylamide) (di-tert-butyldimethylsilylcyclopentadienyl)titanium dichloride, dimethylsilylene(tert-butylamide) (di-tert-butyldimethylsilylcyclopentadienyl)titanium dichloride, dimethylsilylene(phenylamide) (tert-butyldimethylsilylcyclopentadienyl)titanium dichloride, dimethyl-silylene(cyclohexylamide) (tert-butyldimethylsilylcyclopentadienyl)titanium dichloride, dimethylsilylene(methylamide) (phenylcyclopentadienyl) titanium dichloride, dimethylsilylene(ethylamide) (phenylcyclopentadienyl) titanium dichloride, dimethylsilylene(n-propylamide) (phenylcyclopentadienyl) titanium dichloride, dimethylsilylene(isopropylamide) (phenylcyclopentadienyl)titanium dichloride, dimethylsilylene(tert-butylamide) (phenylcyclopentadienyl) titanium dichloride, dimethylsilylene(phenylamide) (phenylcyclopentadienyl) titanium dichloride, dimethylsilylene(cyclohexylamide) (phenylcyclopentadienyl)titanium dichloride, dimethylsilylene(methylamide)(indenyl)titanium dichloride, dimethylsilyleneiethylamide) (indenyl)titanium dichloride, dimethylsllylene(n-propylamide)(indenyl) titanium dichloride, dimethylsilylene(isopropylamide) (indenyl)titanium dichloride, dimethylsilylene(tert-butylamide) (indenyl)titanium dichloride, dimethylsilylene (phenylamide)(indenyl)titanium dichloride, dimethylsilylene(cyclohexylamide),(Indenyl) titanium dichloride, dimethylsilylene(methylamide) (methylindenyl) titanium dichloride, dimethylsilylene(ethylamide) (methylindenyl) titanium dichloride, dimethylsilylene(n-propylamide) (methylindenyl)titanium dichloride, dimethylsilylene(isopropylamide)(methyl indenyl) titanium dichloride, dimethylsilylene(tert-butylamide) (methylindenyl)titanium dichloride, dimethylsilylene (phenylamide)(methylindenyl) titanium dichloride, dimethylsilylene(cyclohexylamide)(methylindenyl) titanium dichloride, dimethylsilylene(methylamide) (phenylindenyl) titanium dichloride, dimethylsilylene (ethylamide)(phenylindenyl)-titanium dichloride, dimethylsilylene(n-propylamide)(phenylindenyl)titanium dichloride, dimethylsilylene(isopropylamide) (phenylindenyl) titanium dichloride, dimethylsilylene(tert-butylamide)(phenylindenyl) titanium dichloride, dimethylsilylene(phenylamide) (phenylindenyl) titanium dichloride, dimethylsilylene(cyclohexylamide) (phenylindenyl) titanium dichloride, etc.

There can also be included compounds wherein dimethylsilylene of these compounds is replaced with diethylsilylene, diphenylsilylene, dimethoxysilylene, methylene, ethylene or isopropylidene; compounds wherein titanium is replaced with zirconium or hafnium; compounds wherein chloride is replaced with bromine, iodide, dimethylamide, diethylamide, n-butoxide or isopropoxide.

[Explanation of each step]

In the preparation of the bridged type transition metal complex represented by the above-mentioned general formula (1), the following step (i) is carried out.

Step (i): a step for reacting a cyclopentadiene compound represented by the above-mentioned general formula (2) with a compound selected from the group consisting of organo-alkaline metal compounds, hydrides of alkaline metal and organomagnesium compounds to produce an alkaline metal salt compound or a magnesium salt compound of a cyclopentadiene compound.

Specific examples of the organo-alkaline metal compounds include organolithium compounds such as methyl lithium, ethyl lithium, n-butyl lithium, sec-butyl lithium, tert-butyl lithium, lithium trimethylsilyl acetylide, lithium acetylide, trimethylsilyl methyl lithium, vinyl lithium, phenyl lithium, allyl lithium; and compounds wherein lithium of these compounds are replaced with sodium, potassium, rubidium or cesium. Alkaline metal compounds having an alkyl group having 1 to 10 carbon atoms are preferred, and lithium, sodium or potassium compounds having an alkyl group having 1 to 10 carbon atoms are more preferred. Alkyl lithium compounds having an alkyl group having 1 to 10 carbon atoms are still more preferred.

The hydride of the alkaline metal includes hydrides of lithium, sodium, potassium, rubidium and cesium, preferably sodium hydride and potassium hydride.

The organomagnesium compound includes dialkyl magnesium compounds or alkyl magnesium halides, and specific examples thereof include diethyl magnesium, diethyl magnesium, di-n-propyl magnesium, diisopropyl magnesium, di-n-butyl magnesium, n-butylethyl magnesium, methyl magnesium iodide, methyl magnesium chloride, isopropyl magnesium chloride, etc. As the alkyl, those having 1 to 10 carbon atoms are preferred. Alkyl magnesium halides are preferred.

Among organo-alkaline metal compounds, hydrides of alkaline metal and organomagnesium compounds, organo-alkaline metal compounds or a hydrides of an alkaline metal are preferred, and alkyl lithiums are more preferred.

The amount of the compound selected from the group consisting of organo-alkaline metal compounds, hydrides of alkaline metal and organomagnesium compound (hereinafter abbreviated to a "metal compound", sometimes) is normally within the range from 1 to 10 mol per mol of the cyclopentadiene compound used in this step(i). When the amount of metal compound is considerably smaller than that of the cyclopentadiene compound (e.g. less than 1 mol), the amount of an alkaline metal or magnesium salt compound of the cyclopentadiene compound (hereinafter abbreviated to a "salt compound", sometimes) is sometime reduced, unfavorably. On the other hand, when the amount of the metal compound is too large (e.g. more than 10 mol), a large amount of a salt compound as an intermediate can be produced but it is uneconomical. On the other hand, when the salt compound produced in this step(i) is fed to the following step without isolation or purification, the metal compound remained in the system is reacted with the transition metal compound, which sometimes results in an unfavorable increase of by-products. The amount is preferably 1.5 to 3 mol, more preferably 1.8 to 2.5 mol, per mol of the cyclopentadiene compound.

The order of the addition of each reagent in the step (i) is not specifically limited, and the metal compound can be added to the cyclopentadiene compound and the addition may also be performed in the reverse manner. The reaction is normally performed in a solvent which is inert to each reagent. Examples of the solvent include aromatic hydrocarbon solvents such as benzene, toluene, xylene, mesitylene, etc.; aliphatic hydrocarbon solvents such as pentane, hexane, heptane, octane, etc.; and ether solvents such as diethyl ether, tetrahydrofuran, etc. These solvents can be used alone or in combination of two or more thereof. The amount is normally within the range from 1- to 200-fold, preferably 3- to 50-fold, based on the weight of the cyclopentadiene compound.

The reaction temperature in the step (i) is not specifically limited, but it is preferably from the temperature higher than $-100$ ° C. to not more than boiling point of the solvent used, more preferably from $-80$ to $150°$ C. Further, from the industrial point of view, it is preferred to carry out at the temperature within the range from $-20$ to $150°$ C., more preferably from $-20$ to $115°$ C., particularly from $-20$ to $80°$ C. In this case, an aliphatic hydrocarbon solvent and/or an aromatic hydrocarbon solvent is preferable since when an ether solvent is used, the metal compound is sometimes reacted with the solvent.

In the present invention, a method of stirring a cyclopentadiene compound and a metal compound at the temperature of less than $10°$ C. while being contacting with each other, and heating to the temperature higher than $10°$ C. after a lapse of a predetermined time (e.g. 30 minutes to 6 hours) is preferable because production of by-products can be controlled. When the reaction proceeds to the following step without isolation and purification after the completion of this step, a smaller amount of by-products are produced in this step, which is better.

In the present invention, the following step (ii) is then carried out, thereby producing the bridged type transition metal complex represented by the above general formula (1).

step (ii): a step of reacting the alkaline metal salt or magnesium salt compound of the cyclopentadiene compound obtained in the step (i) with a transition metal compound represented by the above general formula (3).

More specific examples of the transition metal compound represented by the general formula (3) include titanium halide such as titanium tetrachloride, titanium tetrabromide, titanium tetraiodide, etc.; titanium amide compound such as tetrakis(dimethylamino)titanium, dichlorobis (dimethylamino)titanium, trichloro(dimethylamino) titanium, tetrakis(diethylamino)titanium, etc.; alkoxytitanium compound such as tetraisopropoxytitanium, tetra-n-butoxytitanium, dichlorodiisopropoxytitanium, trichloroisopropoxytitanium, etc.; and compounds wherein titanium of above compounds is replaced with zirconium or hafnium. Transition metal halide compounds are preferred, tetrachlorides of the transition metal are more preferred, and titanium tetrachloride is particularly preferred.

The amount of the transition metal compound is normally within the range from 0.5 to 3.0 mol per mol of the salt compound (alkaline metal salt or magnesium salt of the cyclopentadiene compound). When the amount of the transition metal compound is considerably smaller than that of the salt compound (e.g. less than 0.5 mol), the reaction yield of the bridged type transition metal complex is sometimes lowered, unfavorably. On the other hand, when the amount of the transition metal compound is too large (e.g. more than 3.0 mol), the step of treating the unreacted transition metal compound is sometimes required in a post-treating step (particularly, when the halide of the transition metal is used, an oxidation treatment is required.). The amount is preferably within the range from 0.7 to 1.5 mol per mol of the salt compound.

The order of the addition of each reagent in the step (ii) is not specifically limited, but the transition metal compound can be added to the alkaline metal salt compound or magnesium salt compound of the cyclopentadiene compound and the addition may also be performed in the reverse manner.

The reaction temperature in the step (ii) is preferably from a temperature higher than −100° C. to not more than boiling point of the solvent used, more preferably from −80 to 150° C. The reaction temperature is preferably within the range from −80 to 150° C., which is particularly advantageous from the industrial point of view, more preferably −20 to 150° C., particularly from −20 to 80° C.

The reaction is normally carried out in a solvent which is inert to each reagent. Examples of the solvent include aromatic hydrocarbon solvent such as benzene, toluene, xylene, mesitylene, etc.; and aliphatic hydrocarbon solvent such as pentane, hexane, heptane, octane, etc. When there is no obstacle in the process, an ether solvent such as diethyl ether, tetrahydrofuran, etc. may be used, but the transition metal compound represented by the general formula (3) sometimes causes an unfavorable vigorous exothermic reaction with an ether unfavorably. The solvent is preferably an aliphatic hydrocarbon solvent, an aromatic hydrocarbon solvent, or a mixture thereof.

In the present invention, the salt compound produced in the step (i) can be fed to the step (ii) without isolation or purification, which is preferable because of the resulting excellent final yield. In this case, it is preferred to carry out the step (i) using an aliphatic hydrocarbon solvent, an aromatic hydrocarbon solvent, or a mixture thereof as the solvent.

In the present invention, the bridged type transition metal complex represented by above general formula (1) is produced by the method comprising the above steps (i) and (ii), wherein at least the step (ii) is performed in the presence of an amine compound.

The amine compound used in the present invention is not specifically limited, but primary-, secondary-, or tertiary-amine can be used. The amine compound may be a mono-amine compound, or a polyamine compound having two or more nitrogen atoms. The amine compound may be a chain amine compound or a cyclic amine compound.

Specific examples of the amine compound include primary amine compound such as methylamine, ethylamine, n-propylamine, isopropylamine, n-butylamine, tert-butylamine, n-octylamine, n-decylamine, aniline, ethylenediamine, etc.; secondary amine compound such as dimethylamine, diethylamine, di-n-propylamine, di-n-propylamine, di-n-butylamine, di-tert-butylamine, di-n-octylamine, di-n-decylamine, pyrrolidine, hexamethyldisilazane, diphenylamine, etc.; tertiary amine compound such as trimethylamine, triethylamine, tri-n-propylamine, tri-n-butylamine, diisopropylethylamine, tri-n-octylamine, tri-n-decylamine, triphenylamine, N,N-dimethylaniline, N,N,N',N'-tetramethylethylenediamine, N-methylpyrrolidine, 4-dimethylaminopyridine, etc. Preferably, it is a chain or cyclic secondary amine compound or tertiary amine compound having 1 to 4 nitrogen atoms and 2 to 24 carbon atoms, more preferably tertiary amine compound. Among them, triethylamine of low cost is used, particularly preferably.

The amount of the amine compound is normally not more than 10 mol, preferably from 0.5 to 10 mol, per mol of the salt compound (an alkaline metal salt compound or a magnesium salt compound of cyclopentadiene compound). Although the details of the mechanism are not clear, it is considered that the amine compound interacts with the salt compound to form a complex compound having high solubility (salt compound-amine compound), thereby improving the reaction yield. When the amount of the amine compound is considerably smaller than that of the salt compound (e.g. less than 0.5 mol), the reaction yield is sometimes lowered because the amount of the complex compound produced is reduced, unfavorably. On the other hand, when the amount of the amine compound is too large (e.g. more than 10 mol), the excessive amine compound sometimes reacts with the transition metal compound represented by the general formula (3), unfavorably. The amount of the amine compound is more preferably within the range from 1 to 3 mol per mol of the salt compound.

In the present invention, it is suitable to feed the salt compound produced in the step (i) to the step (ii) without isolation or purification, but in that case, it is possible to add an amine compound at the step (i).

The bridged type transition metal complex represented by above general formula (1), obtained in the step (ii), is isolated by various methods. The complex is preferably isolated by filtering salts produced as by-products in the step (ii) to remove them, followed by recrystallization with a suitable solvent, preferably e.g. an aliphatic hydrocarbon solvent.

EXAMPLE

The present invention is further illustrated in detail with Examples but is not limited thereto.

Example 1

Synthesis of dimethylsilylene(tert-butylamide)(tetramethylcyclopentadienyl)titanium dichloride In a 100 ml four-necked flask equipped with a stirrer under a nitrogen atmosphere, to a solution of 2.00 g (7.97 mmol) of (tert-butylamide)(2,3,4,5-tetramethylcyclopenta-1,3-dienyl)dimethylsilane, 10 g of toluene and 3.38 g (33.7 mmol) of triethylamine, 10.6 ml of a 1.63M hexane solution of n-butyl lithium was slowly added dropwise over 4 hours at 5° C., and the mixture was stirred for 12 hours at 15° C. A uniform solution was obtained. Subsequently, a solution was separately prepared by dissolving 1.62 g (8.53 mmol) of TiCl$_4$ into 5.0 g of toluene under a nitrogen atmosphere, and the solution was cooled to −10° C. Then, the reaction solution prepared previously in the 100 ml four-necked flask was cooled to −10° C. and the TiCl$_4$ solution was slowly added over 2 hours. This reaction solution was slowly heated to room temperature over 1.5 hours and then stirred overnight. The mixture was filtered with Celite and the remained solid was extracted twice with 10 g of toluene per one time. After the filtrate and extracted solution were combined, the solvent was concentrated, followed by recrystallization from hexane to obtain a brown plate crystal in the total amount of 1.11 g. The data of $^1$H-NMR(CDCl$_3$ solvent) and mass spectrum of this brown plate crystal are shown as follows. δ6 0.71(s,6H), 1.44(s,9H), 2.14(s,6H), 2.24(s,6H) Mass spectrum (CI, m/e) 367

From these data of $^1$H-NMR and mass spectrum, the resultant brown plate crystal was identified as dimethylsilylene(tert-butylamide) (tetramethylcyclopentadienyl) titanium dichloride (yield: 38%).

Example 2

In a 100 ml four-necked flask equipped with a stirrer under a nitrogen atmosphere, to a solution of 2.00 g (7.97 mmol) of (tert-butylamide)(2,3,4,5-tetramethylcyclopenta-1,3-dienyl) dimethylsilane, 10 g of toluene and 3.38 g (33.7 mmol) of triethylamine, 15.9 ml of a 1.05M diethyl ether solution of methyl lithium was slowly added dropwise over 4 hours at 5° C., and the mixture was stirred for 12 hours at 15° C. A uniform solution was obtained. Subsequently, the solution was separately prepared by dissolving 1.62 g (8.53 mmol) of TiCl$_4$ into 5.0 g of toluene under a nitrogen atmosphere, and the solution was cooled to −10° C. Then, the reaction solution prepared previously in the 100 ml four-necked flask was cooled to −10° C. and the TiCl$_4$ solution was slowly added over 2 hours. This reaction solution was slowly heated to room temperature over 1.5hours and then stirred overnight. The mixture was filtered with Celite and the remained solid was extracted twice with 10 g of toluene per one time. After the filtrate and extracted solution were combined, the solvent was distilled off, followed by recrystallization from hexane to obtain a brown plate crystal in the total amount of 1.16 g. This brown plate crystal was identified as dimethylsilylene(tert-butylamide) (tetramethylcyclopentadienyl) titanium dichloride (yield: 40%) because the crystal showed the same data as those of Example 1 in $^1$H-NMR(CDCl$_3$) and mass spectrum.

Comparative Example 1

In a 100 ml four-necked flask equipped with a stirrer under a nitrogen atmosphere, to a solution of 2.00 g (7.97 mmol) of (tert-butylamide)(2,3,4,5-tetramethylcyclopenta-1,3-dienyl)dimethylsilane and 10 g of toluene, 10.6 ml of a 1.63M hexane solution of n-butyl lithium was slowly added dropwise over 4 hours at 5° C. and the mixture was stirred for 12 hours at 15° C. A solid was deposited and was in the form of slurry. Subsequently, the solution was separately prepared by dissolving 1.62 g (8.53 mmol) of TiCl$_4$ into 5.0 g of toluene under a nitrogen atmosphere and the solution was cooled to −10° C. Then, the reaction mixture (slurry) prepared previously in the 100 ml four-necked flask was cooled to −10° C. and the TiCl$_4$ solution was slowly added over 2 hours. This reaction mixture was slowly heated to room temperature over 1.5 hours and then stirred overnight. The mixture was filtered with Celite and its solid was extracted twice with 10 g of toluene per one time. After these toluene solutions were combined, the solvent was distilled off, followed by recrystallization from hexane to obtain a brown plate crystal in the total amount of 0.22 g. This brown plate crystal was identified as dimethylsilylene(tert-butylamide) (tetramethylcyclopentadienyl)titanium dichloride (yield: 8%) because the crystal showed the same data as those in Example 1 in $^1$H-NMR(CDCl$_3$) and mass spectrum.

Comparative Example 2

Synthesis was performed according to the method described in JP-A-03-163088.

Into a 100 ml four-necked flask equipped with a stirrer under a nitrogen atmosphere, 26.7 g of tetrahydrofuran was added and the mixture was frozen by using liquid nitrogen. To this frozen mixture, 0.72 g (3.79 mmol) of TiCl$_4$ was added and the solution was heated to −76° C. To this solution, a solution prepared separately by dissolving 1.00 g (3.80 mmol) of dilithium(tert-butylamide)(2,3,4,5-tetramethylcyclopentadienyl) dimethylsilane in 26.7 g of tetrahydrofuran, was added dropwise. This solution was slowly heated to room temperature over 1.5 hours and then stirred overnight. The solvent was evaporated from the resultant very deep colored solution. The residue was extracted with pentane, and the resulting extracted solution was obtained by filtration. The solution was concentrated, followed by recrystallization from pentane to obtain a brown plate crystal in the total amount of 0.14 g. The brown plate crystal was identified as dimethylsilylene(tert-butylamide) (tetramethylcyclopentadienyl)titanium dichloride (yield: 10%) because this brown plate crystal showed the same data as those in Example 1 in $^1$H-NMR(CDCl$_3$) and mass spectrum.

As described above, according to the present invention, there is provided a method for producing a specific bridged type transition metal complex in high yield. In the present invention, since the reaction can be carried out in high yield without using an ether solvent, the solvent replacement is not required and the reaction can be carried out under the industrially advantageous reaction temperature condition of not less than 120° C. Besides, there can be omitted an operation of isolating/purifying an intermediate between two steps. Therefore, the industrial value of the present invention is great.

What is claimed is:

1. A method for producing a bridged type transition metal complex represented by the following general formula (1), comprising the following steps (i) and (ii), wherein at least the step (ii) is performed in the presence of an amine compound;

step (i): a step of reacting a cyclopentadiene compound represented by the following general formula (2) with a compound selected from the group consisting of organic alkaline metal compound, hydride of alkaline metal and organomagnesium compound to produce an alkaline metal salt compound or a magnesium salt compound of the cyclopentadiene compound; and step (ii): a step of reacting the alkaline metal salt compound or magnesium salt compound of the cyclopentadiene compound with a transition metal compound represented by the following general formula (3):

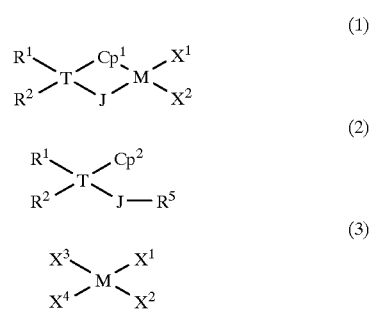

(wherein M represents a transition metal atom of Group IV of the Periodic Table of the Elements; J represents —O—, —S—, —NR$^3$— or —PR$^4$—(wherein R$^3$ and R$^4$ independently represent a hydrogen atom, an alkyl group having 1 to 20 carbon atoms optionally substituted with a halogen, vinyl group, an alkoxy group having 1 to 20 carbon atoms, an aralkyloxy group having 7 to 20 carbon atoms or an aryloxy group having 6 to 20 carbon atoms, an aralkyl group having 7 to 20 carbon atoms optionally substituted with a halogen, vinyl group, an alkoxy group having 1 to 20 carbon atoms, an aralkyloxy group having 7 to 20 carbon atoms or an aryloxy group having 6 to 20 carbon atoms, an aryl group having 6 to 20 carbon atoms optionally substituted with a halogen, vinyl group, an alkoxy group having 1 to 20 carbon atoms, an aralkyloxy group having 7 to 20 carbon atoms or an aryloxy group having 6 to 20 carbon atoms, or a silyl group having 1 to 20 carbon atoms optionally substituted with a halogen, vinyl group, an alkoxy group having 1 to 20 carbon atoms, an aralkyloxy group having 7 to 20 carbon atoms or an aryloxy group having 6 to 20 carbon atoms); T represents an atom of Group XIV of the Periodical Table of the Elements; $Cp^1$ represents a group having a cyclopentadiene type anion skeleton; $X^1$, $X^2$, $X^3$, $X^4$, $R^1$ and $R^2$ independently represent a hydrogen atom, a halogen atom, an alkyl group having 1 to 20 carbon atoms optionally substituted with a halogen, vinyl group, an alkoxy group having 1 to 20 carbon atoms, an aralkyloxy group having 7 to 20 carbon atoms or an aryloxy group having 6 to 20 carbon atoms, an aralkyl group having 7 to 20 carbon atoms optionally substituted with a halogen, vinyl group, an alkoxy group having 1 to 20 carbon atoms, an aralkyloxy group having 7 to 20 carbon atoms or an aryloxy group having 6 to 20 carbon atoms, an aryl group having 6 to 20 carbon atoms optionally substituted with a halogen, vinyl group, an alkoxy group having 1 to 20 carbon atoms, an aralkyloxy group having 7 to 20 carbon atoms or an aryloxy group having 6 to 20 carbon atoms, a silyl group having 1 to 20 carbon atoms optionally substituted with a halogen, vinyl group, an alkoxy group having 1 to 20 carbon atoms, an aralkyloxy group having 7 to 20 carbon atoms or an aryloxy group having 6 to 20 carbon atoms, an alkoxy group having 1 to 20 carbon atoms optionally substituted with a halogen, vinyl group, an alkoxy group having 1 to 20 carbon atoms, an aralkyloxy group having 7 to 20 carbon atoms or an aryloxy group having 6 to 20 carbon atoms, an aralkyloxy group having 7 to 20 carbon atoms optionally substituted with a halogen, vinyl group, an alkoxy group having 1 to 20 carbon atoms, an aralkyloxy group having 7 to 20 carbon atoms or an aryloxy group having 6 to 20 carbon atoms, an aryloxy group having 6 to 20 carbon atoms optionally substituted with a halogen, vinyl group, an alkoxy group having 1 to 20 carbon atoms, an aralkyloxy group having 7 to 20 carbon atoms or an aryloxy group having 6 to 20 carbon atoms, a sulfonyloxy group having 1 to 20 carbon atoms or a di-substituted amino group having 2 to 20 carbon atoms; $X^1$ and $X^2$ and/or $R^1$ and $R^2$ may optionally combine with each other to form a ring; $Cp^2$ represents a group having a cyclopentadiene skeleton; $R^5$ represents a hydrogen atom, an alkyl group having 1 to 20 carbon atoms optionally substituted with a halogen, vinyl group, an alkoxy group having 1 to 20 carbon atoms, an aralkyloxy group having 7 to 20 carbon atoms or an aryloxy group having 6 to 20 carbon atoms, an aralkyl group having 7 to 20 carbon atoms optionally substituted with a halogen, vinyl group, an alkoxy group having 1 to 20 carbon atoms, an aralkyloxy group having 7 to 20 carbon atoms or an aryloxy group having 6 to 20 carbon atoms, an aryl group having 6 to 20 carbon atoms optionally substituted with a halogen, vinyl group, an alkoxy group having 1 to 20 carbon atoms, an aralkyloxy group having 7 to 20 carbon atoms or an aryloxy group having 6 to 20 carbon atoms or a silyl group having 1 to 20 carbon atoms optionally substituted with a halogen, vinyl group, an alkoxy group having 1 to 20 carbon atoms, an aralkyloxy group having 7 to 20 carbon atoms or an aryloxy group having 6 to 20 carbon atoms).

2. The method according to claim 1, wherein the amine compound is a secondary amine compound or a tertiary amine compound.

3. The method according to claim 2, wherein the amine compound is triethylamine.

4. The method according to claim 1, wherein the compound selected from the group consisting of organo-alkaline metal compounds, hydrides of alkaline metal and organomagnesium compounds is an organo-alkaline metal compound or a hydride of an alkaline metal.

5. The method according to any one of claim 1, wherein a solvent is used in the reactions of the steps (i) and (ii) and the solvent is an aliphatic hydrocarbon solvent and/or an aromatic hydrocarbon solvent.

6. The method according to claim 4, wherein a solvent is used in the reactions of the steps (i) and (ii) and the solvent is an aliphatic hydrocarbon solvent and/or an aromatic hydrocarbon solvent.

7. The method according to claim 1, wherein the reactions of the steps (i) and (ii) are carried out at the reaction temperture of −20 to 80° C.

8. The method according to claim 4, wherein the reactions of the steps (i) and (ii) are carried out at the reaction temperature of −20 to 80° C.

9. The method according to claim 5, wherein the reactions of steps (i) and (ii) are carried out at the reaction temperature of −20 to 80° C.

10. The method according to claim 1, wherein T is a silicon atom.

11. The method according to claim 4, wherein T is a silicon atom.

12. The method according to claim 5, wherein T is a silicon atom.

13. The method according to claim 1, wherein J is —$NR^3$— (wherein $R^3$ is defined above).

14. The method according to claim 1, wherein $X^1$, $X^2$, $X^3$ and $X^4$ independently represent a hydrogen atom, a halogen atom, an alkoxy group having 1 to 20 carbon atoms optionally substituted with a halogen, vinyl group, an alkoxy group having 1 to 20 carbon atoms, an aralkyloxy group having 7 to 20 carbon atoms or an aryloxy group having 6 to 20 carbon atoms, an aralkyloxy group having 7 to 20 carbon atoms optionally substituted with a halogen, vinyl group, an alkoxy group having 1 to 20 carbon atoms, an aralkyloxy group having 7 to 20 carbon atoms or an aryloxy group having 6 to 20 carbon atoms, an aryloxy group having 6 to 20 carbon atoms optionally substituted with a halogen, vinyl group, an alkoxy group having 1 to 20 carbon atoms, an aralkyloxy group having 7 to 20 carbon atoms or an aryloxy group having 6 to 20 carbon atoms or a sulfonyloxy group having 1 to 20 carbon atoms.

15. The method according to claim 1, wherein the amount of the compound selected from the group consisting of organo-alkaline metal compounds, hydrides of alkaline metal and organomagnesium compound is within the range of from 1 to 10 mol per mol of the cyclopentadiene compound used in step (i).

16. The method according to claim 15, wherein the range is 1.5 to 3 mol per mol of the cyclopentadiene compound used in step (i).

17. The method according to claim 1, wherein the transition metal compound of formula (3) is a transition metal halide.

18. The method according to claim 1, wherein the transition metal compound of step (ii) is present in the range of 0.5 to 3.0 mol per mol of the alkaline metal salt or magnesium salt compound.

19. The method according to claim 1, wherein the amine compound is present in the range of 1 to 3 mol per mol of the alkaline metal salt or magnesium salt compound.

20. The method according to claim 4, wherein the organo-alkaline metal compound is an alkyl lithium compound.

* * * * *